United States Patent [19]
Duerr et al.

[11] Patent Number: 5,823,776
[45] Date of Patent: Oct. 20, 1998

[54] ENOSSAL SINGLE TOOTH IMPLANT WITH TWISTING PREVENTION

[75] Inventors: Walter Duerr, Remchingen; Axel Kirsch, Stuttgart, both of Germany

[73] Assignee: IMZ Fertigungs- und Vertiebsgellschaft fur dentale Technologie mbH, Filderstadt, Germany

[21] Appl. No.: 701,688

[22] Filed: Aug. 22, 1996

[30] Foreign Application Priority Data

Sep. 20, 1995 [DE] Germany .................. 195 34 979.2

[51] Int. Cl.⁶ .................................................. A61C 8/00
[52] U.S. Cl. ................................................... 433/173
[58] Field of Search .................. 433/172, 173, 433/174

[56] References Cited

U.S. PATENT DOCUMENTS

| | | | |
|---|---|---|---|
| 4,960,381 | 10/1990 | Niznick . | |
| 5,000,686 | 3/1991 | Lazzara et al. | 433/174 |
| 5,078,607 | 1/1992 | Niznick | 433/174 |
| 5,125,840 | 6/1992 | Dürr et al. . | |
| 5,195,892 | 3/1993 | Gersberg | 433/174 |
| 5,199,873 | 4/1993 | Schulte et al. | 433/174 |
| 5,449,291 | 9/1995 | Lueschen et al. | 433/173 |
| 5,577,912 | 11/1996 | Prins | 433/173 |
| 5,620,323 | 4/1997 | Bressman et al. | 433/174 |

FOREIGN PATENT DOCUMENTS

| | | | |
|---|---|---|---|
| 4022753 | 1/1992 | Germany | 433/174 |
| 41 27 839 | 3/1992 | Germany . | |
| 4127436 | 3/1992 | Germany | 433/173 |
| 4238383 | 7/1994 | Germany | 433/174 |
| 413 224 | 12/1966 | Switzerland . | |
| 9406367 | 3/1994 | WIPO | 433/173 |
| 9420043 | 9/1994 | WIPO | 433/173 |

*Primary Examiner*—Ralph A. Lewis
*Attorney, Agent, or Firm*—Hill & Simpson

[57] ABSTRACT

An enossal single tooth implant for a tightly fitting dental prosthesis comprises a substantially cylindrical base body insertable in a bore made in a jaw bone and having a blind bore extending inward from one end for receiving a plug portion of a spacing sleeve with the spacing sleeve and the blind bore having an arrangement of coacting elements to prevent a twisting therebetween. The coacting elements include at least one axially extending groove and at least one axially extending projection with each groove being located immediately adjacent the outer edge of the base body and with each projection being adjacent a shoulder of the spacing sleeve which shoulder is engaged on the outer edge of the base body when the sleeve is mounted thereon. In addition to the positive elements, the plug portion has a cylindrical guiding portion followed by a cylindrical centering portion of a smaller diameter. The blind bore of the basic body also has stepped portions of different diameters with the largest diameter being adjacent the open end and forming a guiding surface for the guiding portion of the sleeve and followed by a smaller diameter portion forming the centering portion.

19 Claims, 2 Drawing Sheets

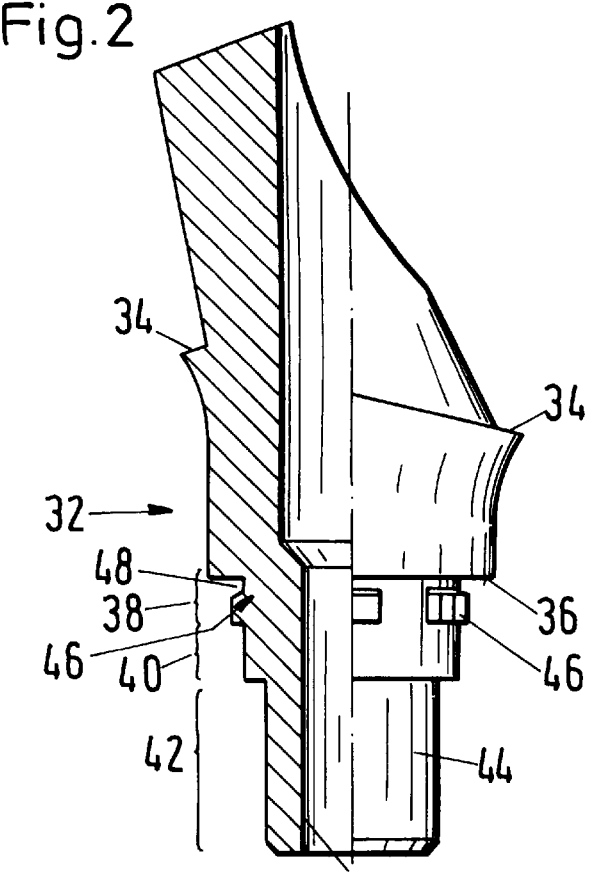
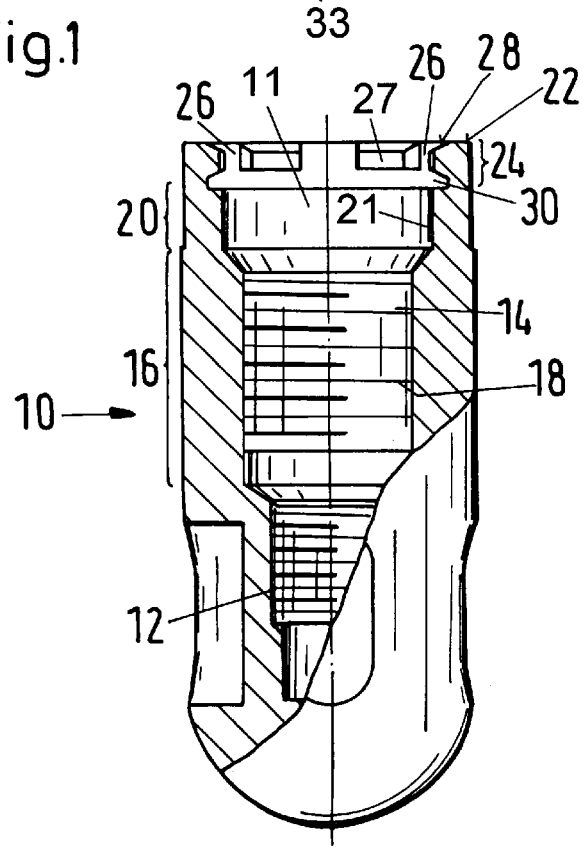

ENOSSAL SINGLE TOOTH IMPLANT WITH TWISTING PREVENTION

BACKGROUND OF THE INVENTION

The present invention is directed to an enossal single tooth implant for tightly fitting a dental prosthesis which implant includes a base body, that is insertable in a bore made in a jawbone and a spacing sleeve attachable to the base body. The base body has a blind bore open on one end which is a coronal end and closed at the opposite end. The spacing sleeve is attachable in a twisting prevented manner to the coronal end of the base body and has a reduced diameter centering collar which is insertable into the hollow cylindrical annular recess formed by a blind bore in the base body adjacent the coronal end while a shoulder of the sleeve is received on the outer edge of the body at the coronal end. The spacing sleeve has a bore that extends through the centering collar and is open on its coronal end for the reception of an implant post. The connection device for the twist preventing connection of the spacing sleeve is formed with the hollow cylindrical annular recess of the basic body having at least one circumferentially acting basic body positive connection element and the centering collar of the spacing sleeve has at least one spacing sleeve positive connecting element complimentary to the basic body positive connecting elements. The implant post will directly or indirectly be insertable into the blind bore of the base and at least partially traverse the spacing sleeve and the fastening head for the dental prosthesis.

In a single tooth implant of this type such as disclosed in U.S. Pat. No. 5,125,840, whose disclosure is incorporated by reference thereto and which claims priority for German application 4 028 885 and from German patent application P 195 09 762.9-32, the twisting prevention was undertaken in that the basic body had a positive connecting elements which were provided on the bottom of an annular recess of the basic body and the spacing sleeve positively connecting elements which were complimentary thereto are on the lower front edge of the centering collar of the spacing sleeve. From a manufacturing standpoint such positive connection elements are relatively difficult to produce. In certain uses, the location of these positive connection elements was undesirable since the full depth of the annular recess or the full length of the centering collar is not available for centering, fixing and securing of the spacing sleeve relative to the basic body.

In U.S. Pat. No. 4,960,381, other difficulties of a similar nature occur in the enossal dental implant. The difficulties are due to the fact that the positive connection elements of the basic body are spaced from the coronal front edge within a blind bore of the basic body.

SUMMARY OF THE INVENTION

The object of the prevent invention is to develop a single tooth implant wherein the case of improved manufacturing possibilities and even precise guidance and centering of the spacing sleeve in the basic body is ensured.

To accomplish these objects, the present invention is directed to a single tooth implant having a basic body, a spacing sleeve and means for preventing twisting therebetween. The basic body has a blind bore forming a coronal end for the body and has a positive connection area adjacent the coronal end followed by a guide portion with a cylindrical surface and then a centering area with a diameter smaller than the cylindrical surface of the guide portion. The spacing sleeve has a fastening end spaced from a plug portion by an annular shoulder. The plug portion adjacent the shoulder has a positive connecting portion on a cylindrical portion followed by a guidance portion with a cylindrical surface and a centering portion with a cylindrical surface with a smaller diameter than the cylindrical surface of the guidance portion. The diameter of the cylindrical surface of the guidance portion matches the diameter of the guide portion of the blind bore while the diameter of the centering portion matches the diameter of the centering area of the blind bore. The means for preventing twisting includes positive connecting elements in the positive connecting portion and positive connecting area with the elements including at least one groove and at least one projection receivable in the groove when the plug portion is inserted into the blind bore with the annular shoulder engaging the end face of the coronal end.

The centering body of the basic body can be provided with internal threads. The invention optionally provides for the internal threads being cervically connected to the centering area of the basic body and the threads are disposed inward toward the closed end of the basic body.

Another embodiment of the invention is characterized in that the implant post completely traverses the spacing sleeve and can be screwed into internal threads close to a cervical or closed end of the basic body.

It is also possible according to the invention for at least one of the basic body positive connection elements to have the form of a coronally open positive connection groove extending parallel to the longitudinal axis of the basic body.

The invention also proposes that the positive connection grooves have in a radial plane, which extends perpendicular to the axis of the bore, a basic substantial circular segmental cross section. The positive connection grooves can have a substantially triangular cross section in a radial plane which extends perpendicular to the axis of the bore in the basic body. The invention optionally proposes that the positive connection grooves in a radial plane which extends perpendicular to the axis of the bore in the basic body has an approximately rectangular-curved cross section. According to the invention the positive connection grooves can be opened toward the closed or cervical end.

It is also possible according to the present invention for the positive connection grooves to have a decreasing cross section from adjacent the coronal end towards the closed end of the basic body. The invention also proposes the cross section of the positive connection grooves decreases radially from the coronal and to the closed end of the basic body. The basic body connection elements can have a 30° spacing with respect to the basic body circumference.

The invention also proposes that the basic body positive connection elements have a 60° spacing with respect to the basic body circumference.

According to the invention it is also possible for the number of positive connection elements of the spacing sleeve to be smaller than the number of positive connection elements of the basic body.

Another embodiment of the invention is characterized in that the positive connection area of the basic body has an annular undercut between the positive connection elements of the basic body and the guidance area.

It is also possible according to the present invention for the end wall at the coronal end of the basic body to have a bevel or chamfer tapering conically inward from the front edge of the basic body into the vicinity of the basic body positive connection elements.

The invention also proposes the positive connecting portion of the centering collar has an annular undercut between the shoulder and the connection elements.

The invention is based on the surprising finding that it is possible to improve a single tooth implant which has proved satisfactory in practice in that the positive connection elements of the basic body are positioned directly adjacent to or at the coronal front edge and with the corresponding arrangement and construction of the spacing sleeve positive connection elements complimentary thereto. Due to the fact that the complete depth of the annular recess of the basic body is available for the centering and guidance of the spacing sleeve there is a significantly improved stability of the connection between the spacing sleeve and basic body. Moreover, the arrangement of the positive connecting elements in the circumferential wall of the annular recess formed by the blind bore of the basic body or the centering collar of the spacing sleeve allows a greater design freedom with regard to the nature of the spacing and also the shaping of the positive connecting elements.

Other advantages and features will be readily available from the following description of the preferred embodiments, the drawings and claims.

BRIEF DESCRIPTION OF THE DRAWINGS

FIG. 1 is a partial longitudinal cross sectional view with portions in elevation for purposes of illustration of a basic body of an enossal single tooth implant according to the present invention;

FIG. 2 is a partial cross sectional view with portions in elevations for purpose of illustration of a spacing sleeve with a fastening head for a dental prosthesis for the single tooth implant of FIG. 1;

DESCRIPTION OF THE PREFERRED EMBODIMENTS

Figure 3A:
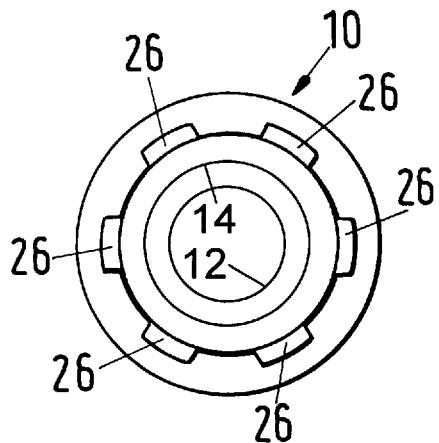
FIG. 3a is an end view of the basic body of FIG. 1.

The principles of the present invention are particularly useful when incorporated into a single tooth implant of an embodiment of the basic body generally indicated at 10 in FIG. 1 which acts with a spacing sleeve generally indicated at 32 in FIG. 2. The basic body 10 is of a known type such as disclosed in the above-mentioned U.S. Pat. No. 5,125, 840.

The basic body 10, which is closed at its one end or cervical end which is at the bottom of FIG. 1 has towards a coronal end at the top an open blind bore 11. Near the closed end, the blind bore 11 is provided with internal threads 12 with a relatively small diameter in which can be screwed an implant post which is not shown in FIG. 1 and which will be discussed hereinafter. To the internal threads 12 of the basic body 10 is connected in the coronal direction an annular cylindrical portion 14 with a larger diameter than the internal threads 12. The annular or cylindrical portion 14 has internal threads 18 and forms a centering area 16 which is connected to the internal threads 12. To the centering area 16 of the cylindrical portion 14 is coronally connected a guidance area 20 which is a cylindrical larger diameter portion than the centering area 16 and has a smooth, hollow cylindrical inner wall 21. From the guidance area 20 to the coronal front edge 22 of the basic body 10 is a positive connection area 24 of the bore 11 in which there are several positive connecting elements in the form of axially extending grooves 26 in an inner wall 27. From the front edge 22 to the positive connecting area 24 of the bore 11 has a bevel or chamfer 28 tapering conically in the direction of the cervical or closed end and extending into the vicinity of the positive connecting grooves 26. Between the guidance area 20 and the positive connecting elements or groove 26 there is an annular undercut 30 which facilitates a chip deposition-free production of the positive connecting elements or grooves 26.

The spacing sleeve 32 as shown in FIG. 2 serves in this manner described in the German patent application P 195 09 762.9-32 and has a fastening head for a not shown, tightly fitting dental prosthesis and is provided with an all around attachment shoulder 34 for the prosthesis which may be a crown of a tooth. The spacing sleeve 32 has an annular shoulder 36 which connects the fastening end to a stub or plug portion which is received in the blind bore 11 of the basic body 10. The stub or plug portion has immediately adjacent the shoulder 36 a positive connection portion 38 followed by a guidance portion 40 and a centering portion 42 which will be received in the blind bore with the shoulder 36 engaging the front edge 22. The positive connection area 38 has a plurality of axially directed positive connection noses 46 whose shape and arrangement but not necessarily the number corresponds to the positive connection grooves 26 of the basic body 10. The positive connection area 38 of the spacing sleeve 32 is provided with an annular undercut 48 between the shoulder 36 and the positive connecting noses 46 and this facilitates the chip deposition during manufacture of the positive connecting noses 46.

When inserting the spacing sleeve 32, which is provided with the axial longitudinal bore 33 whose internal diameter corresponds to the external diameter of a not shown implant post, is inserted in the basic body 10, the centering portion 421 which is formed by a cylindrical centering collar 44, will be engaged in the centering area 16 of the annular portion 14 so that a smooth cylindrical circumferential surface of the centering portion 42 comes to rest on the inner boundaries of the internal threads 18 of the centering area 16 of the basic body 10. At the same time, the guidance portion 40 of the spacing sleeve 32 is located with a press fit in the guidance area 22 of the basic body 10 and the positive connection noses 42 engage in the positive connection grooves 26 while the shoulder 36 comes to rest on the front edge 22. Therefore, the spacing sleeve 32 is connected to the basic body 40 in a twist preventing manner. By means of the implant post traversing the spacing sleeve 32 and being screwed into the internal threads 12 of the basic body 10, the spacing sleeve 32 can be firmly connected to the basic body 10. In an embodiment other than those shown in FIG. 1 and 2 the internal threads 18 of the basic body 10 can have a different constructed spacing sleeve for threading in for example a two part sleeve as is shown in the above mentioned U.S. Pat. No. 5,125,840.

Figure 3B:
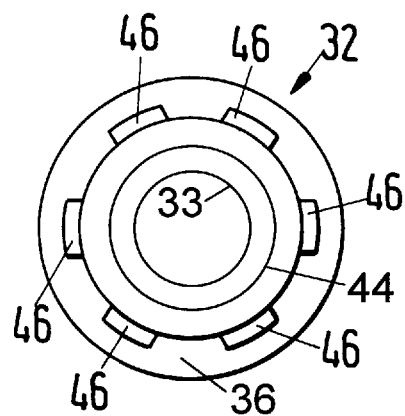
FIG. 3b is an end view of a spacing sleeve of FIG. 2.
Figure 4A:
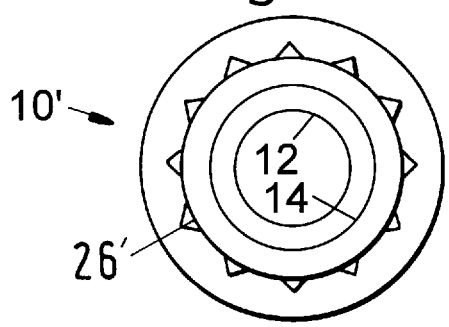
FIG. 4a is an end view of a first modification of the basic body of FIG. 1.
Figure 4B:
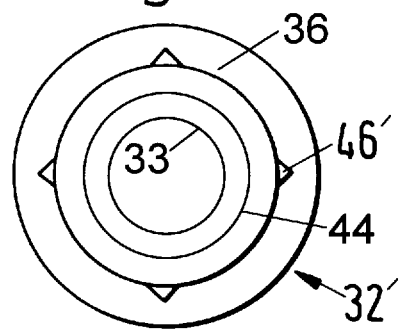
FIG. 4b is an end view of a first modification of the spacing sleeve of FIG. 2.

As shown in FIG. 3a, the positive connecting area of the basic body 10 has six equally spaced, axial positive connecting grooves 26 which in the represented embodiment have a cross sectional shape of a rectangle with a substantially tangential directed but also curved longitudinal edges and have an annular spacing of 60° between centers of adjacent grooves. In FIG. 3b, the spacing sleeve 32 in the embodiment of FIGS. 1 and 2 is provided with six equally spaced, axial positive connecting noses 46. In the embodiments of FIGS. 4a and 4b, the basic body 10' in FIG. 4a has twelve positive connecting grooves 26' with an equal annular spacing of 30° and in FIG. 4b the spacing sleeve 32' is only provided with four positive connecting noses 46'. The positive connecting grooves 26' and the positive connecting noses 46' have in this case a triangular cross section in a plane perpendicular to the longitudinal axes of the basic body and of the spacing sleeve. It is pointed out that the spacing sleeve 32' has only four positive connecting noses 46 which have a 90° annular spacing therebetween.

Figure 5A:
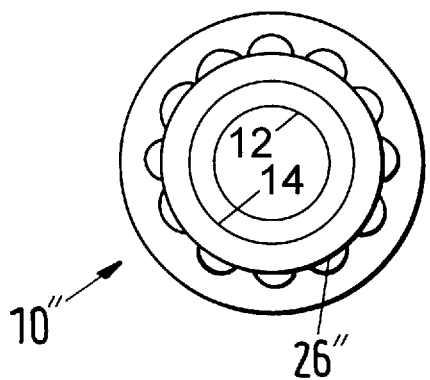
FIG. 5a is an end view of the second modification of the basic body of FIG. 1.
Figure 5B:
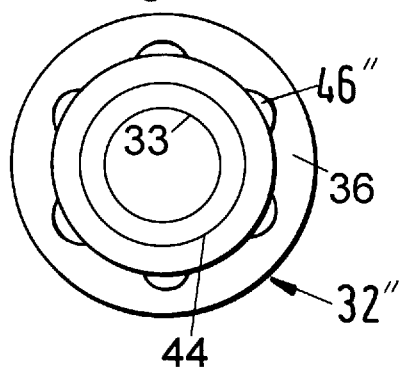
FIG. 5b is a second modification of the spacer sleeve of FIG. 2.

In the embodiment of FIGS. 5a and 5b, the basic body 10" of FIG. 5a has twelve positive connecting grooves 26" with a 30° spacing and the grooves 26" have a circular segmental cross section in a plane perpendicular to the longitudinal axis of the basic body 10". According to FIG. 5b, the spacing sleeve 32" is provided with six positive connecting noses 46" each having a corresponding cross section to the cross section of the grooves 26".

As a function of the spacing or the spacing ratio of the basic body 10' and 10" relative to the spacing sleeves 32' and 32", the spacing sleeves 32' and 32" can be inserted in different rotational positions within their respective basic bodies 10' and 10". Thus, the treating surgeon has a number of desired positions available to him as far as orienting the spacing sleeve such as 32' relative to the basic body 10'.

Although modifications and changes may be suggested by those versed in the art, it should be understood that we wish to embody within the scope of the patent granted herein all such modifications that reasonably and properly come within the scope of our contribution to the art.

We claim:

1. A single tooth implant for a tightly fitting dental prosthesis, said implant comprising:

a substantially cylindrical basic body insertable in a bore made in a jaw bone, said basic body having an axially extending blind bore extending from one end towards a second end to provide the body with a closed end at said second end and said one end having a coronal front edge extending between an outside surface of the basic body and the blind bore, a spacing sleeve having an axially extending passage being attachable to the coronal front edge of the basic body by means of an implant post insertable through the passage and into the blind bore, and means for preventing twisting between the spacing sleeve and the basic body, said blind bore of said basic body having a positive connection area adjacent the one end comprising at least one connecting element followed by a guidance area of a cylindrical surface which has a first diameter and merges into a centering area of a second diameter smaller than the first diameter, said spacing sleeve having a plug portion separated from a fastening end adapted for receiving the prosthesis by an annular shoulder receivable on the coronal front edge when the sleeve is mounted on the basic body with the plug portion inserted into the blind bore, said plug portion adjacent the annular shoulder having a positive connecting portion with at least one connecting element, a guidance portion spaced from the positive connecting portion towards an end of the plug portion and then a centering portion adjacent the end of the plug portion, said guidance portion of the plug portion having an outer diameter essentially matching the first diameter of the guidance area and said centering portion of the plug portion having an outer diameter essentially matching the second diameter of the centering area, said centering portion being receivable in the centering area of the blind bore of the basic body with the guidance portion received in the guidance area of the blind bore and the positive connection portion being disposed in the positive connection area of the blind bore as the shoulder of the spacing sleeve engages the coronal front edge, said means for preventing twisting comprising the connecting element of one of the sleeves and basic body being a groove and the connecting element of the other of the sleeve and the basic body being a projection receivable in said groove when the plug portion of the sleeve is inserted in the blind bore with the annular shoulder engaging the coronal front edge.

2. A single tooth implant according to claim 1, wherein the centering area of the blind bore is provided with threads.

3. A single tooth implant according to claim 1, wherein the blind bore includes a threaded portion of a third diameter smaller than the second diameter between the centering area and the closed end of the basic body.

4. A single tooth implant according to claim 3, wherein the implant post completely traverses the spacing sleeve and can be threaded into the threaded portion close to the closed end of the basic body.

5. A single tooth implant according to claim 1, wherein each connecting element of the basic body has a shape of a positive connecting groove open toward said one end and extending parallel to the longitudinal axis of the basic body.

6. A single tooth implant according to claim 5, wherein each positive connecting groove has a substantially circular segmental cross section in a plane extending perpendicular to the axis of the blind bore of the basic body.

7. A single tooth implant according to claim 5, wherein each positive connecting groove has a substantially triangular cross section in a plane extending perpendicular to the axis of the blind bore.

8. A single tooth implant according to claim 5, wherein each positive connecting groove has an approximately rectangular-curved cross section in a plane extending perpendicular to the axis of the line bore.

9. A single tooth implant according to claim 5, wherein each positive connecting groove is open toward the closed end of the basic body.

10. A single tooth implant according to claim 5, wherein each positive connecting groove has a decreasing cross section from the one end towards the closed end of the blind bore.

11. A single tooth implant according to claim 10, wherein the cross section of said positive connecting groove decreases radially from the one end to the closed end of the blind bore.

12. A single tooth implant according to claim 1 wherein the basic body has a plurality of connecting elements, said connecting elements being spaced around the circumference of the blind bore of the basic body with an annular spacing of 30° therebetween.

13. A single tooth implant according to claim 1, wherein the basic body has a plurality of connecting elements, said elements being spaced around a circumference of the blind bore with a 60° spacing therebetween.

14. A single tooth implant according to claim 1, wherein the basic body has a plurality of connecting elements spaced around a periphery of the blind bore and the spacing sleeve has a plurality of connecting elements spaced around the positive connecting portion with the number of elements of the spacing sleeve being less than the number of elements for the basic body.

15. A single tooth implant according to claim 1, wherein the positive connection area of the basic body has an annular undercut between each connecting element and the guidance area.

16. A single tooth implant according to claim 1, wherein an inner end wall of the basic body at the one end has a bevel tapering conically towards the closed end from the coronal front edge of the basic body into the positive connection area of the basic body.

17. A single tooth implant according to claim 1, wherein the spacing sleeve has an annular undercut between the annular shoulder and each connecting element.

18. A single tooth implant for a tightly fitting dental prosthesis, said implant comprising:

a substantially cylindrical basic body insertable in a bore made in a jaw bone, said basic body having an axially extending blind bore extending from one end toward a second end to provide the body with a closed end at said second end, said blind bore having a first cylindrical surface portion of a first diameter forming a guidance area followed by a second cylindrical portion of a second diameter smaller than the first diameter forming a centering area followed by a third portion of a third diameter smaller than the second diameter forming a threaded portion, said one end of the basic body having a front edge between the outer surface of the basic body and the blind bore;

a spacing sleeve with an axially extending passage being attachable to the front edge of the basic body by means of an implant post insertable through the passage and into the blind bore, said spacing sleeve having a plug portion separated from a fastening end adapted for receiving the prosthesis by an annular shoulder receivable on the front edge when the sleeve is mounted on the basic body with the plug portion inserted into the blind bore, said plug portion adjacent an end having a centering portion having an outer diameter essentially matching the second diameter of the centering area and having a guidance portion between the centering portion and said annular shoulder having an outer diameter essentially matching the first diameter of the guidance area; and means for preventing twisting between the spacing sleeve and the basic body, said means including the basic body having a positive connecting area having cylindrical surface portions of the first diameter adjacent the one end comprising at least one connecting element and said spacing sleeve having a positive connecting portion with at least one connecting element adjacent the annular shoulder, the connecting element of one of the sleeve and basic body being a groove and the connecting element of the other of the sleeve and basic body being a projection receivable in said groove when the plug portion of the sleeve is inserted into the blind bore with the annular shoulder engaging the front edge and said centering portion being receivable in the centering area of the blind bore of the basic body with the guidance portion received in the guidance area of the blind bore.

19. A single tooth implant according to claim 18, wherein the first cylindrical surface portion and the second cylindrical portion have a combined axial length greater than the first diameter.

\* \* \* \* \*